US005205019A

United States Patent [19]

Schnlichter et al.

[11] Patent Number: 5,205,019

[45] Date of Patent: Apr. 27, 1993

[54] APPARATUS FOR SEPARATING METAL BODIES FROM A TEXTILE FIBER STREAM

[75] Inventors: Stefan Schnlichter, Viersen; Ferdinand Leifeld, Kempen, both of Fed. Rep. of Germany

[73] Assignee: Trützschler GmbH & Co. KG, Mönchengladbach, Fed. Rep. of Germany

[21] Appl. No.: 760,989

[22] Filed: Sep. 17, 1991

[30] Foreign Application Priority Data

Sep. 17, 1990 [DE] Fed. Rep. of Germany ....... 4029412

[51] Int. Cl.[5] ....................... D01G 9/08; D01G 23/00; B07C 5/344; G01N 33/36

[52] U.S. Cl. ....................................... 19/200; 19/205; 137/875; 209/552; 209/571; 241/79; 406/159; 406/168

[58] Field of Search ....................... 19/2, 21, 23, 65 A, 19/66 R, 145.5, 200, 204, 205, 300, 80 A, 105; 209/555, 546, 570, 23, 29; 364/470; 137/875

[56] References Cited

U.S. PATENT DOCUMENTS 3,370,327 2/1968 Van Doorn .......................... 19/205
3,588,685 6/1971 Fallenius .............................. 324/41
3,588,686 6/1971 Lingmann ....................... 209/111.8
4,041,762 8/1972 Shurtleff ........................ 137/875 X
4,167,803 9/1979 Teichmann .............................. 19/2
4,171,262 10/1979 Lattmann et al. ............. 209/270 X
4,400,850 8/1983 Burnett .................................. 19/23
4,480,753 11/1984 Thomas et al. ................. 209/270 X
4,657,144 4/1987 Martin et al. ....................... 209/546

(List continued on next page.)

FOREIGN PATENT DOCUMENTS 0019092 6/1953 Fed. Rep. of Germany .
0941213 4/1956 Fed. Rep. of Germany .
1134262 8/1962 Fed. Rep. of Germany .
1174917 12/1965 Fed. Rep. of Germany .
1980303 7/1967 Fed. Rep. of Germany .
1945316 3/1971 Fed. Rep. of Germany .
2032993 1/1972 Fed. Rep. of Germany .
2252595 5/1973 Fed. Rep. of Germany .
2508067 9/1975 Fed. Rep. of Germany .
2842203 4/1980 Fed. Rep. of Germany .
0153587 1/1982 Fed. Rep. of Germany ...... 209/570

(List continued on next page.)

OTHER PUBLICATIONS

Patent Abstract of Japan, Detector of Iron Piece, Application No. 55-43549, Apr., 1980.

*Primary Examiner*—Clifford D. Crowder
*Assistant Examiner*—Ismael Izaguirre
*Attorney, Agent, or Firm*—Spencer, Frank & Schneider

[57] ABSTRACT

An apparatus for separating foreign bodies from a stream of fiber material includes a vertical chute having an upper inlet and a lower outlet; a mechanism for introducing the fiber material into the chute inlet; and a detector positioned in the chute for emitting a sensor signal upon passage of a foreign body. The fiber material is propelled from the detector towards the chute outlet substantially solely by gravity. The apparatus further has a waste discharge opening provided in the chute between the detector and the chute outlet; a deflecting mechanism arranged in the chute and having first and second positions. In the first position the deflecting mechanism causes the stream of fiber material to proceed in the chute to and through the chute outlet and in the second position the deflecting mechanism causes the stream of fiber material to proceed through the waste discharge opening. The deflecting mechanism is moved from the first position into the second position in response to a sensor signal emitted by the detector.

21 Claims, 8 Drawing Sheets

U.S. PATENT DOCUMENTS

| | | | |
|---|---|---|---|
| 4,685,569 | 8/1987 | Osaki et al. | 209/571 |
| 4,707,887 | 11/1987 | Leifeld et al. | 19/2 |
| 4,736,493 | 4/1988 | Haass-Zöllick et al. | 19/200 |
| 4,778,061 | 10/1988 | Williams | 209/552 X |
| 4,805,266 | 2/1989 | Leifeld et al. | 19/2 |
| 4,848,590 | 7/1989 | Kelly | 209/564 |
| 4,858,277 | 8/1989 | Pinto et al. | 19/200 |
| 4,863,040 | 9/1989 | Sandi | 209/570 |
| 4,977,645 | 12/1990 | Hösel | 19/205 X |
| 5,123,144 | 6/1992 | Demuth et al. | 19/80 R X |

FOREIGN PATENT DOCUMENTS

| | | | |
|---|---|---|---|
| 3411860 | 10/1985 | Fed. Rep. of Germany . | |
| 0231140 | 12/1985 | Fed. Rep. of Germany . | |
| 3615020 | 11/1986 | Fed. Rep. of Germany . | |
| 3533390 | 3/1987 | Fed. Rep. of Germany . | |
| 3708188 | 9/1988 | Fed. Rep. of Germany . | |
| 3900450 | 7/1990 | Fed. Rep. of Germany . | |
| 3931579 | 9/1990 | Fed. Rep. of Germany . | |
| 0045869 | 4/1979 | Japan | 209/571 |
| 3152418 | 6/1988 | Japan | 19/205 |
| 3274863 | 11/1988 | Japan | 19/80 R |
| 0122973 | 1/1959 | U.S.S.R. | 209/571 |
| 1236024 | 6/1986 | U.S.S.R. | 19/205 |
| 1339178 | 9/1987 | U.S.S.R. | 19/80 R |
| 1246844 | 9/1971 | United Kingdom | 209/570 |
| 2096190 | 10/1982 | United Kingdom | 19/205 |
| 2200374 | 8/1988 | United Kingdom | 19/205 |
| 2203174 | 10/1988 | United Kingdom . | |
| 2249323 | 9/1990 | United Kingdom | 19/205 |

APPARATUS FOR SEPARATING METAL BODIES FROM A TEXTILE FIBER STREAM

CROSS REFERENCE TO RELATED APPLICATION

This application claims the priority of German Application No. P 40 29 412.9 filed Sep. 17, 1990, which is incorporated herein by reference.

BACKGROUND OF THE INVENTION

1. Technical Field

This invention relates to an apparatus for separating foreign bodies, particularly metal foreign bodies, from a textile fiber stream advanced in a fiber processing line. In a conventional separating apparatus, the fiber material (fiber tufts) is pneumatically conveyed in a duct which has a branch-off location provided with a deflecting mechanism for the foreign bodies. A metal detector is situated upstream of the branch-off location as viewed in the travelling direction of the fiber tufts. The deflecting mechanism and the metal detector are operatively coupled with a control device in such a manner that the deflecting mechanism is, as a result of a response signal from the metal detector upon passage of a metal foreign body, switched to a position in which the fiber stream is guided to a waste collector.

2. Background Art

In a known apparatus, as disclosed in European Patent Application 033 a long, closed pneumatic fiber tuft conveying duct includes a metal detector and a branch-off location which is connected to a waste removing conduit in which a complex vacuum generating device—which requires its own compressor—is arranged for generating the suction stream that transports the fiber tufts. Apart from the expensive arrangement, the system is disadvantageous in that a complex collecting device for the separated material is needed in the region of the closed pneumatic transport system which further requires additional gates for material removal.

SUMMARY OF THE INVENTION

It is an object of the invention to provide an improved apparatus of the above-outlined type from which the discussed disadvantages are eliminated and which, in particular, is of simple construction and in which the distance between the metal detector and the deflecting mechanism is shortened as compared to prior art constructions.

This object and others to become apparent as the specification progresses, are accomplished by the invention, according to which, briefly stated, the apparatus for separating foreign bodies from a stream of fiber material includes a vertical chute having an upper inlet and a lower outlet; a mechanism for introducing the fiber material into the chute inlet; and a detector positioned in the chute for emitting a sensor signal upon passage of a foreign body. The fiber material is propelled from the detector towards the chute outlet substantially solely by gravity. The apparatus further has a waste discharge opening provided in the chute between the detector and the chute outlet; a deflecting mechanism arranged in the chute and having first and second positions. In the first position the deflecting mechanism causes the stream of fiber material to proceed in the chute to and through the chute outlet and in the second position the deflecting mechanism causes the stream of fiber material to proceed through the waste discharge opening. The deflecting mechanism is moved from the first position into the second position in response to a sensor signal emitted by the detector.

Thus, according to the invention, downstream of a separator assembly (such as a condenser) for the tuft/air mixture and below the exit location for the fiber material a foreign body detector is arranged which is followed in the vertical direction by a separating gate. If in the operative position, the separating gate deflects the free-falling material, together with the foreign body contained therein, from its normal path of conveyance.

It is an advantage of the invention that the sensing and the separating operations are performed externally of pneumatic ducts or channels.

It is an important feature of the invention to provide for a free fall of the material and to arrange the detector at or close to the location where the free fall starts. The separating gate is arranged spaced from the detector in the direction of free fall. In this manner, the reaction time for the gate is changed by several orders of magnitude which is realized with simple gates without the need of long distances between the detector and the location of separation. For example, the separating gate may be pivoted within 0.5 seconds after receipt of an electric actuating pulse. During such period the foreign body has moved in a free fall only approximately 1.2 m and has a velocity of approximately 4.4 m/sec s that the separating process may be controlled in a simple manner with the apparatus structured according to the invention. It is a further advantage of the construction according to the invention that in contrast to prior art arrangements, a complex and expensive collecting device for the separated material in the region of the closed pneumatic transport system is no longer necessary. Further, an expensive vacuum-generating device may also be dispensed with. It is of particular advantage that a long conveying track of, for example, 8–10 m between the detector and the deflecting device is also no longer necessary. The apparatus according to the invention is operationally reliable because it is based on a fail-safe free fall of the fiber material and the foreign bodies.

DESCRIPTION OF THE PREFERRED EMBODIMENTS

Figure 1:
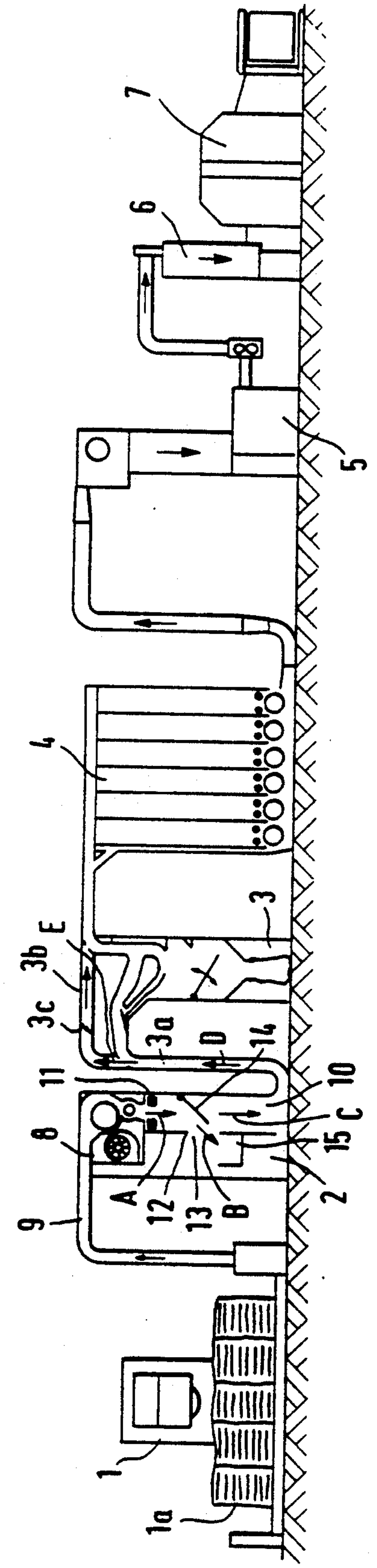
FIG. 1 is a schematic side elevational view of a fiber processing line—including cleaning and carding machines incorporating the invention.

Turning to FIG. 1, there is illustrated therein a fiber processing (cleaning) line which receives fiber tuft material detached from fiber bales 1a by a bale opener 1 which may be, for example, a BLENDOMAT BDT model, manufactured by Trützschler GmbH & Co. KG, Mönchengladbach, Germany. Between the bale opener 1 and a multiple fiber tuft blender 4 there is situated the apparatus 2 according to the invention, followed by a heavy particle separator 3. The multiple blender 4 is followed in the downstream direction by a fine opener 5, and a plurality of card feeders 6 each associated with a carding machine 7 (only a single feeder-and-card assembly is shown). The fiber tufts detached by the bale opener 1 from the fiber bales ia are conveyed pneumatically in a duct 9 to a condenser 8 which is provided with a screening drum. From the condenser 8 there extends a vertical chute 10, the bottom of which opens into a pneumatic duct for advancing material to consecutive processing machines. The chute 10 and the other, downstream-arranged machines are connected to one another with respective pneumatic ducts. No pneumatic conveying duct is provided between the condenser 8 and the chute 10.

In the chute 10, vertically underneath the condenser 8 a metal detector coil 11 is arranged. The fiber material A drops from the condenser 8 through the detector coil 11 and a guide element 12 of the chute 10 in a free fall as indicated by the arrow C. Between the guide element 12 and the chute 10 a discharge opening 13 is provided, adjacent which, on the opposite wall of the chute 10, a pivotal gate 14 is mounted which serves as a deflecting member. An upwardly open waste container 15 is arranged laterally of the chute 10 and underneath the discharge opening 13. As soon as the gate 14 pivots into its operative position (shown in FIG. 1) in response to a sensor signal from the detector coil 11, the fiber material, together with the sensed foreign body, is deflected into the waste container 15, as indicated by the arrow B.

Downstream of the apparatus 2 a heavy particle separator 3 is arranged which may be a SEPAROMAT model, manufactured by Trützschler GmbH & Co. KG, Mönchengladbach, Germany. The separator 3 has an intake channel 3a to which there is coupled an end of an air branch-off conduit 3b so that air quantities indicated by the arrow E in the air branch conduit 3b may be set by a throttle gate 3c as a function of the air quantities (arrow D) flowing through the intake channel 3a. The intake channel 3a is a rising pneumatic conduit between the apparatuses 2 and 3.

Figure 2:
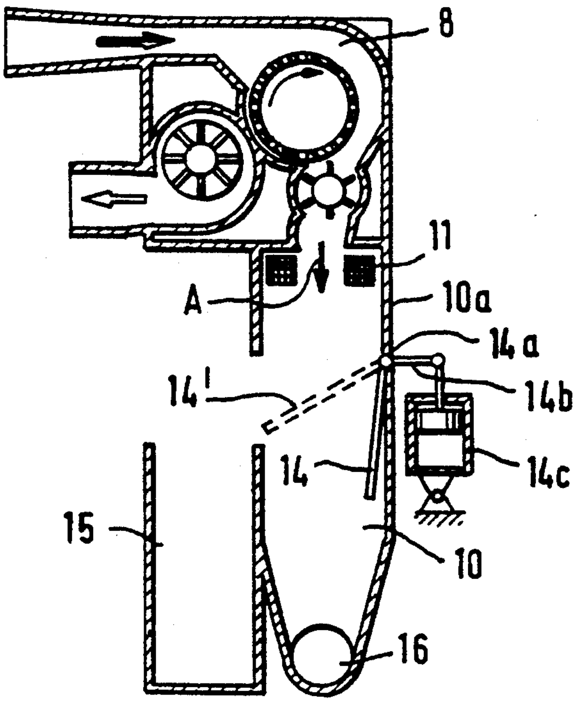
FIGS. 2–6, 7*a*, 7*b* and 8*a* are schematic side elevational views of seven preferred embodiments of the invention.

In FIG. 2, the detector coil 11 is mounted on a non-illustrated holder underneath the condenser 8. The fiber material A drops in a free fall in the chute 10 and is pneumatically carried away through a suction pipe 16 at the bottom of the chute 10. The deflector gate 14 lies flush against the wall 10a of the chute 10 during normal passage of the fiber material and upon generation of a signal by the detector coil 11, responding to the passage of a metallic foreign body, the deflector gate 14 is pivoted away from its flush position with the chute wall 10a into the phantom-line position 14'. The gate 14 is secured to the wall 10a by a pivot 14a to which there is connected one end of a crank lever 14b, whose other end is operatively connected with a pneumatic cylinder 14c which, in turn, is coupled with the detector coil 11 with the intermediary of a control device as will be discussed in connection with FIG. 4.

Figure 3:
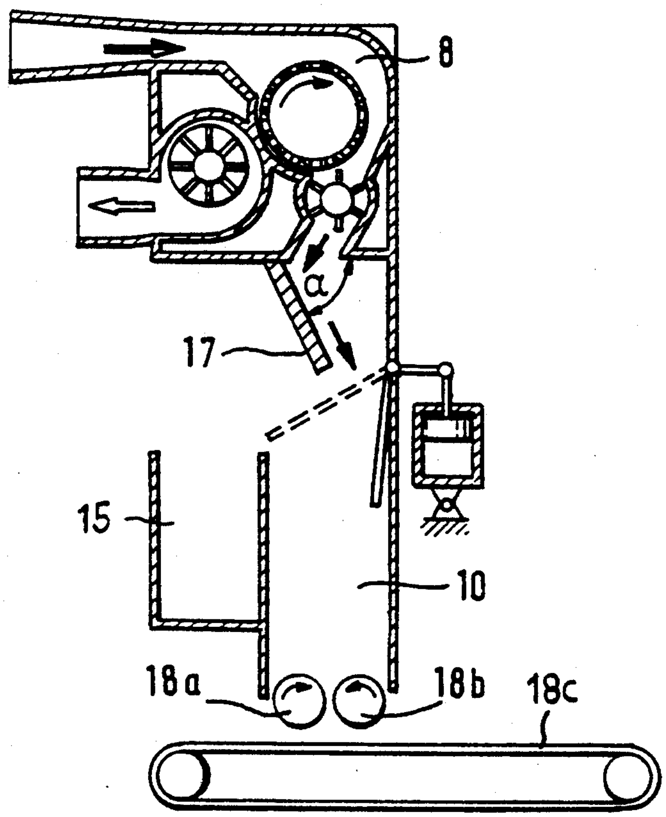

In FIG. 3, underneath the condenser 8 a detector plate 17, containing a plurality of inductive detector coils, is arranged at an angle $\alpha$ to the horizontal. The chute 10 has at its lower end two slowly rotating, cooperating delivery rolls 18a, 18b which remove the fiber material from the chute 10 and cause the fiber material to fall on a removal conveyor 18c.

Figure 4:
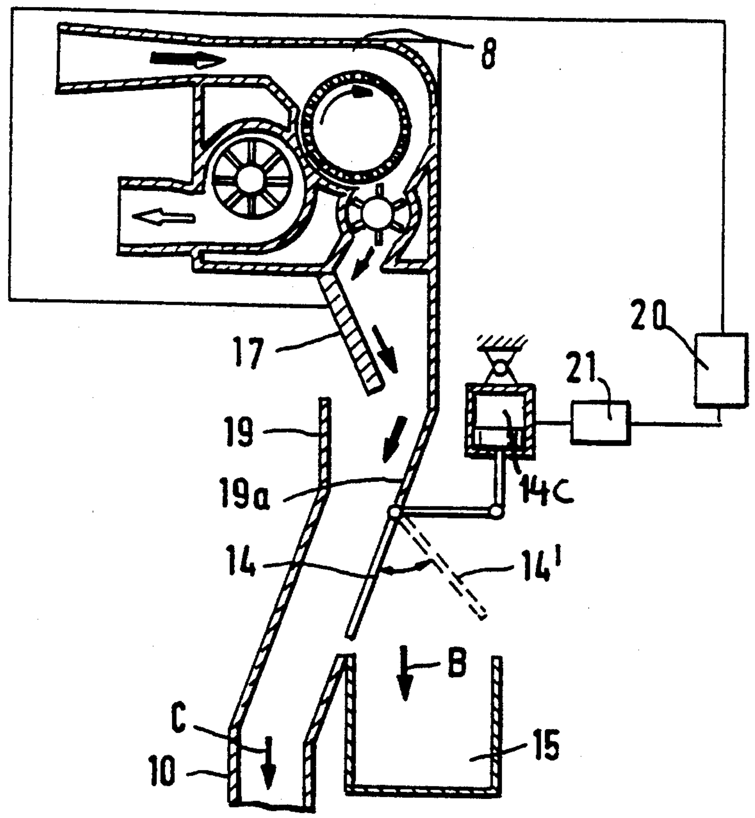

Turning to FIG. 4, underneath the condenser 8 an obliquely oriented detector plate 17 and an obliquely oriented wall 19a of a guide element 19 are provided. The guide element opens into the chute 10. The wall 19a supports the pivotal deflector gate 14. Upon rotation of the gate 14 into its phantom-line position 14', a branch-off aperture in the wall 19a is opened, through which the material passes, together with the metal foreign bodies, and falls into the waste container 15. In their travel from the condenser 8 downwardly, the fiber material and the foreign body are exposed exclusively to gravitational forces. The detector plate 17 is electrically connected with a control device 20 which, in turn, is coupled to the pressure cylinder 14c with the intermediary of a transducer 21.

Figure 5:
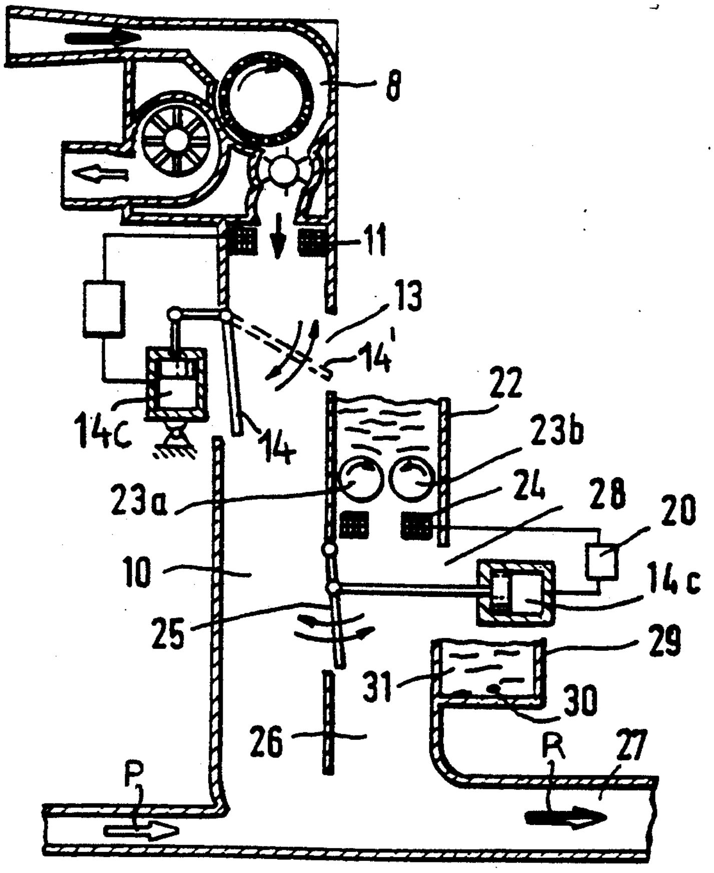

In FIG. 5, underneath the branch-off aperture 13 and adjacent the chute 10 a fiber tuft accumulator 22 is arranged. At the bottom of the fiber tuft accumulator 22 two slowly rotating delivery rolls 23a, 23b are mounted. Underneath the delivery rolls 23a, 23b a further detector coil 21 and a pivotal gate 25 as well as a chute 26 are provided. The chute 26 and the chute 10 open into a common suction duct 27. Between the tuft accumulator 22 and the chute 26 an opening 28 is provided under which a waste container is arranged. In this embodiment two separating devices are serially connected to ensure that the useful fiber quantities 31 which are separated out with the metal foreign body 30 are maintained small. Thus, in operation, the coil 11 generates a signal as a metal foreign body passes therethrough, together with useful fiber material. In response, the cylinder 14c places the pivotal gate 14 into its phantom-line position 14' whereupon the fiber material, together with the metal foreign body, falls into the fiber tuft accumulator 22. Thereafter, the gate 14 is returned into its solid-line position whereupon the fiber material dropping from the condenser 8 may fall through the chute 10 into the pneumatic duct 27 to combine with the air stream P into an air/fiber stream R. Parallel to this operation, the slowly rotating delivery rolls 23a, 23b at the bottom of the accumulator 22 advance the material through the sensor coil 24 and as the earlier collected metal foreign body passes through the coil 24 the latter causes energization of the pressure piston 14c' whereupon the gate 25 is pivoted counterclockwise, thus closing the channel 26 and deflecting the fiber material, together with the metal foreign body, through the opening 28 into the waste collector 29.

Figure 6:
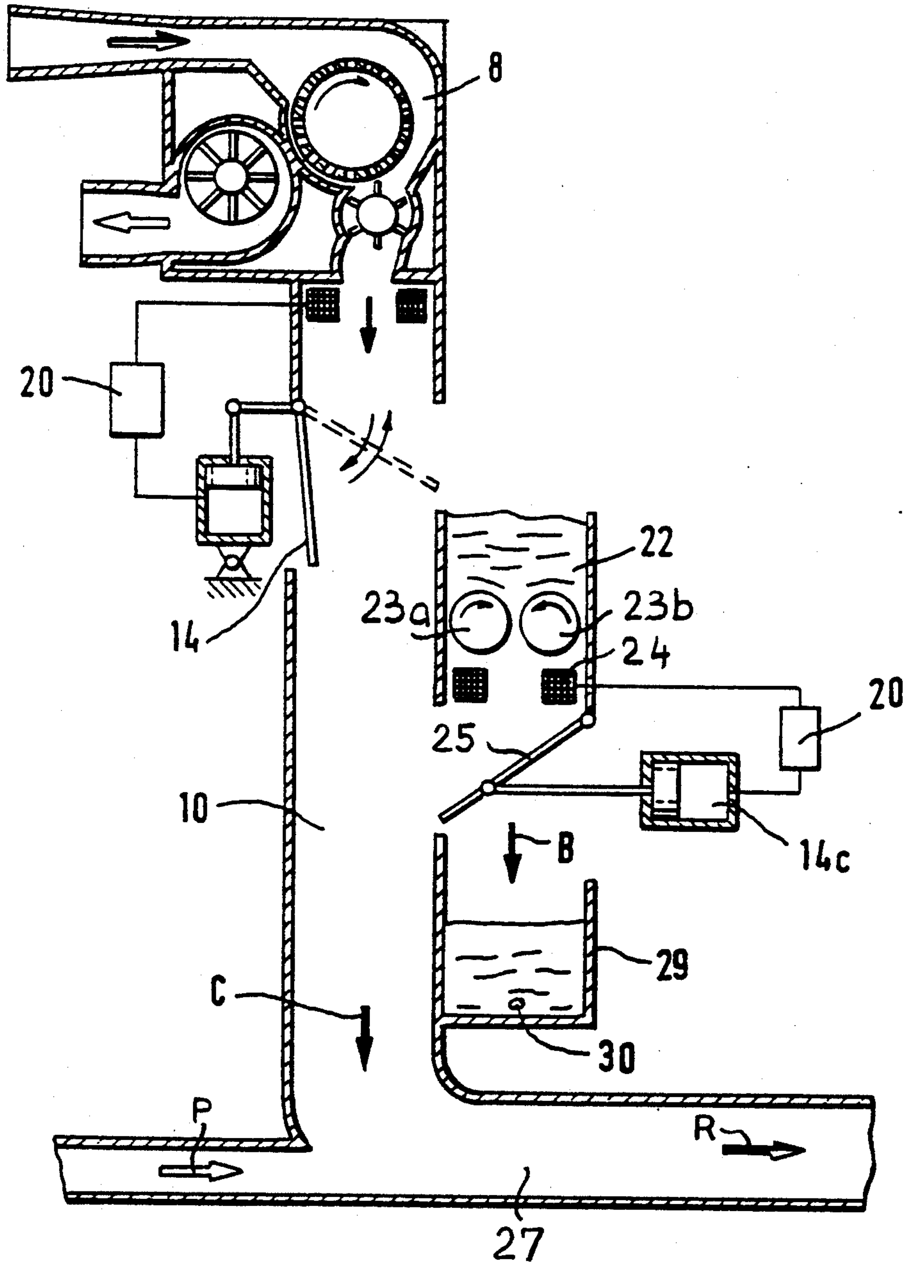

The embodiment illustrated in FIG. 6 is similar to that of FIG. 5 except that in the normal position of the gate 25 the fiber material advanced by the delivery rolls 23a, 23b is deflected into the chute 10 at a location below the gate 14, whereas in the non-illustrated operative position, that is, when the gate 25 is pivoted counterclockwise in response to a sensor signal from the coil 24, the gate 25 allows the fiber material, together with the metal foreign body 30 to fall, as indicated at B, vertically into the waste container 29 situated vertically below the sensor coil 24.

Figure 7A:
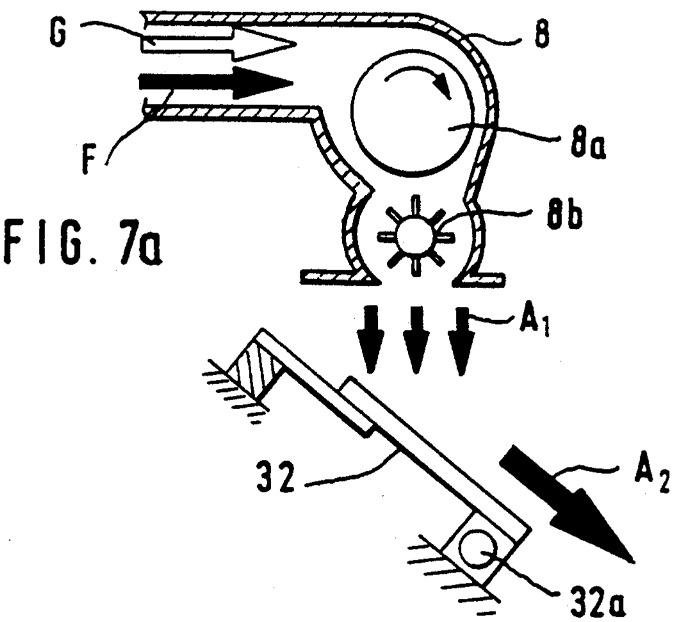
Figure 7B:
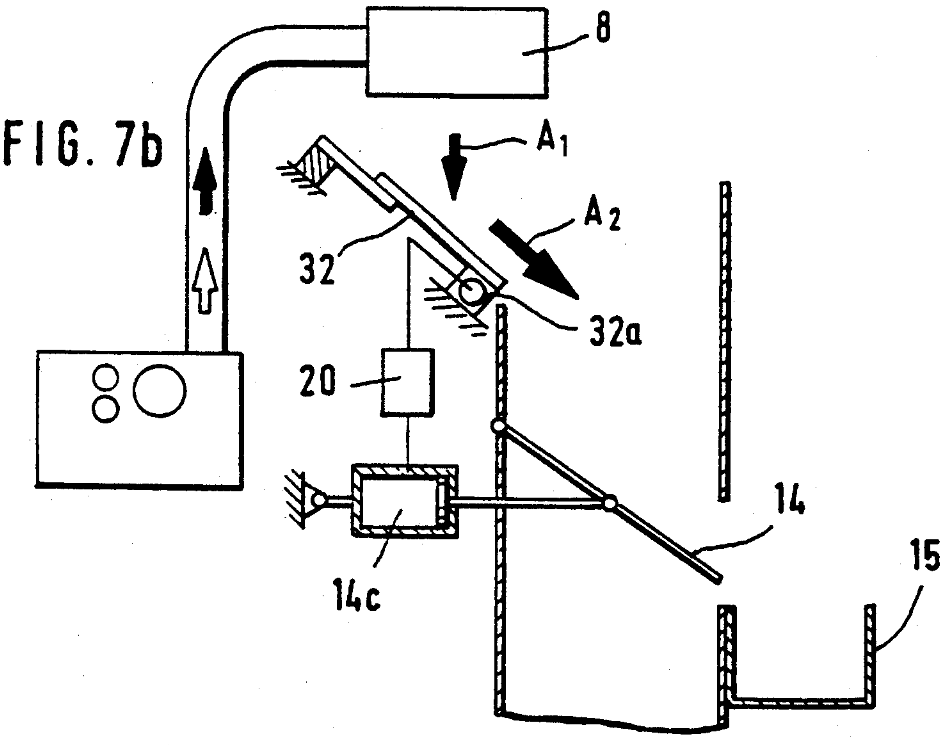

Turning to FIG. 7*a*, underneath the condenser 8 which includes a screening drum **8*a* and a vaned dispenser wheel 8*b*, there is mounted an obliquely oriented weighing plate 32 connected with a weighing cell 32*a*. The fiber stream $A_1$ impinges on the weighing plate 32** and is deflected thereby as a fiber stream $A_2$. FIG. 7*b* shows that the weighing cell **32*a* is connected to the control device 20 which, in turn, is coupled to the pneumatic cylinder 14*c* that operates the gate 14 to guide the fiber material, together with the sensed metal foreign body, into the waste conveyor 15 when a predetermined excess weight is sensed by the weighing plate 32**.

Figure 8A:
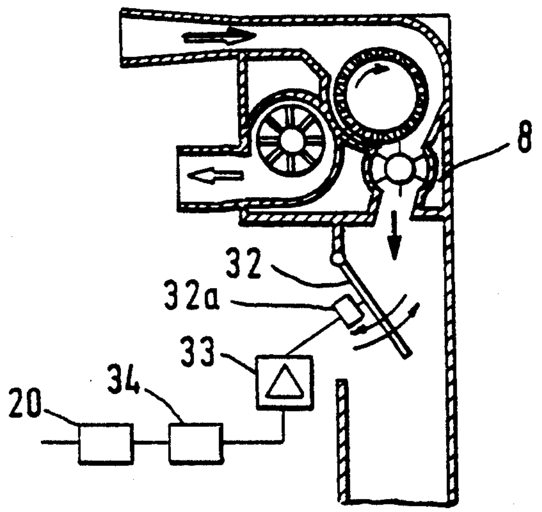

In FIG. 8*a*, between the weighing cell **32*a* which may, for example, comprise expansion measuring strips, and the control device 20 an electric amplifier 33 and an evaluating device 34 are connected. The evaluating device 34 sums in an analog manner the electric signals emitted by the weighing cell 32*a* for the purpose of determining the weight of the fiber tufts and/or heavy foreign bodies impinging on the weighing plate 32**. When a predetermined limit pulse amplitude or energy is reached, the heavy body separating device is triggered as described in connection with FIG. 7*b*.

Figure 8B:
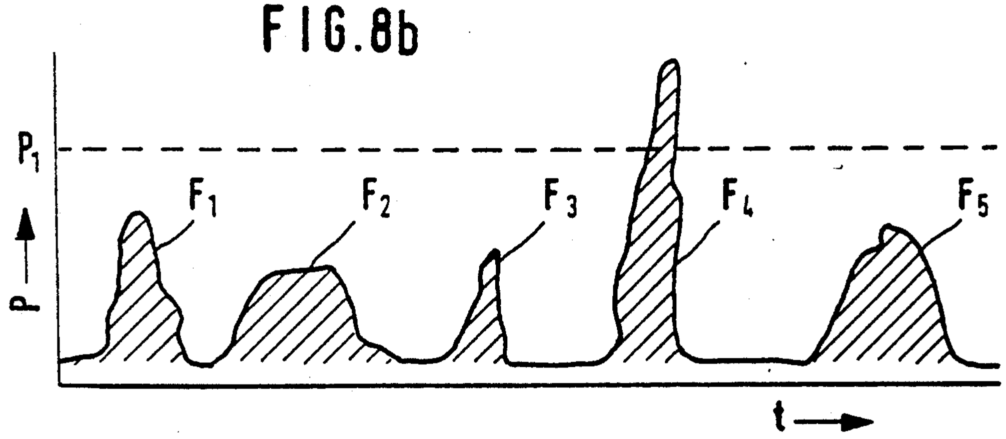
FIG. 8*b* is a diagram illustrating an impact force/time function.
Figure 8C:
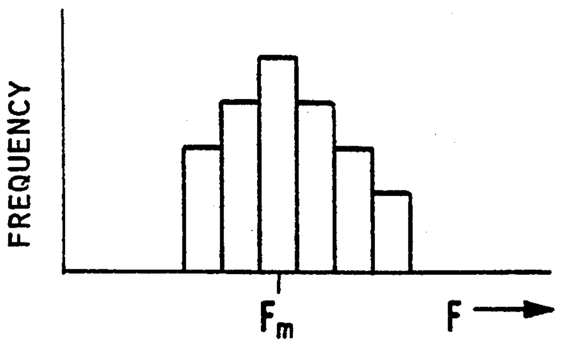
FIG. 8*c* is a diagram illustrating the frequency of fiber tuft size occurrences.

The evaluating device 34 may be so structured that not only the total weight is evaluated but also the under-the-curve areas of the individual coherent pulse signals are statistically evaluated as shown in FIGS. 8*b* and 8*c*. This additionally permits a determination of the fiber tuft sizes and the degree of the opening of the fiber tufts.

In the diagram illustrated in FIG. 8*b* the force P applied to the weighing plate 32 is shown over time t. P1 designates a threshold value for the heavy particle separation. The force signal corresponding to F4 triggers the foreign body separation.

The sum of the areas $F_1$–$F_5$ under the curve corresponds to the fiber tuft weight. The magnitude of each area under the curve, for example, $F_1$ is proportional to the tuft size, that is, to the degree of opening of the fiber tuft. FIG. 8*c* shows a diagram which illustrates the occurrence frequency as a function of the tuft size F. $F_m$ designates the mean fiber tuft size corresponding to the mean fiber tuft weight.

Figure 9:
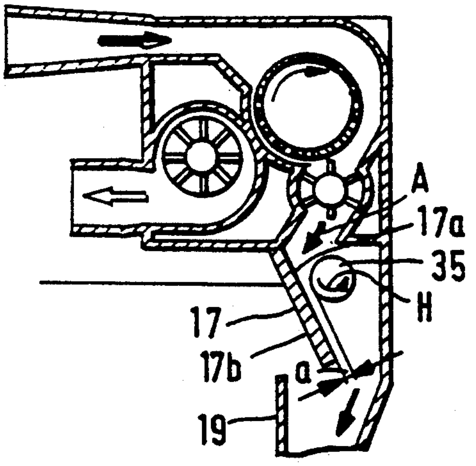
FIG. 9 is a schematic side elevational view of yet another preferred embodiment of the invention.

Turning to FIG. 9, there is shown therein an embodiment similar to that illustrated in FIG. 4, except that the surface **17*a* of the detector plate 17 oriented towards the fiber tufts A is situated at a distance a of a horizontally supported plastic roller 35 which is rapidly rotating in the direction of the arrow H. The fiber material A passes through the gap a and is pressed by the surface of the roller 35 against the face 17*a* of the detector plate 17. Instead of a plastic roller 35 an endless belt 36 may be provided which is supported by end rollers 35'**.

Figure 10:
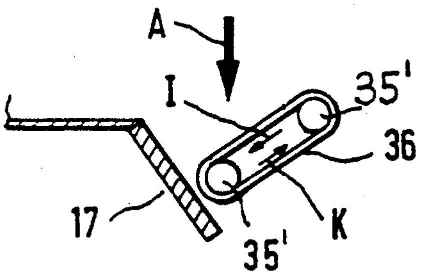
FIG. 10 is a schematic side elevational view of a modified detail of the structure illustrated in FIG. 9.

The detector plate 17 in FIGS. 9 and 10 is a surface sensor which contains a plurality of inductive sensor elements **17*b*** which generate on their active surfaces a high-frequency electromagnetic field that changes as any metal part passes by. For generating such a field there is provided a coil of a high-frequency oscillator, embedded in a ferrite core. If a metal part enters into the field generated by the coil, in the metal part eddy currents appear which cause an energy loss in the field. The energy loss dampens the amplitude of the oscillation of the field, and this phenomenon is converted into a definite electric switching signal.

Figure 11:
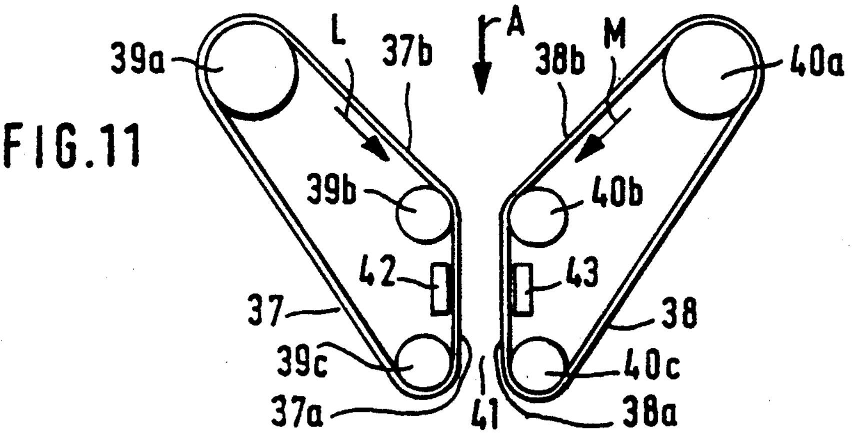
FIG. 11 is a schematic side elevational view of the construction of the apparatus in the zone of a metal detector.

In FIG. 11, there are provided two cooperating conveyor belts 37, 38 trained about support rollers **39*a*, 39*b*, 39*c* and 40*a*, 40*b*, 40*c*, respectively. The belt portions between the support rollers 39*b*, 39*c* and 40*b*, 40*c* define a narrow channel 41 through which the fiber material A passes after the free fall. At the inside of the belt portion an area pressure sensor 42 and 43 is arranged. By virtue of the narrow channel 41, the fiber material A, together with any foreign body, is brought into the sensitive operational range of the sensors 42, 43**.

Figure 12:
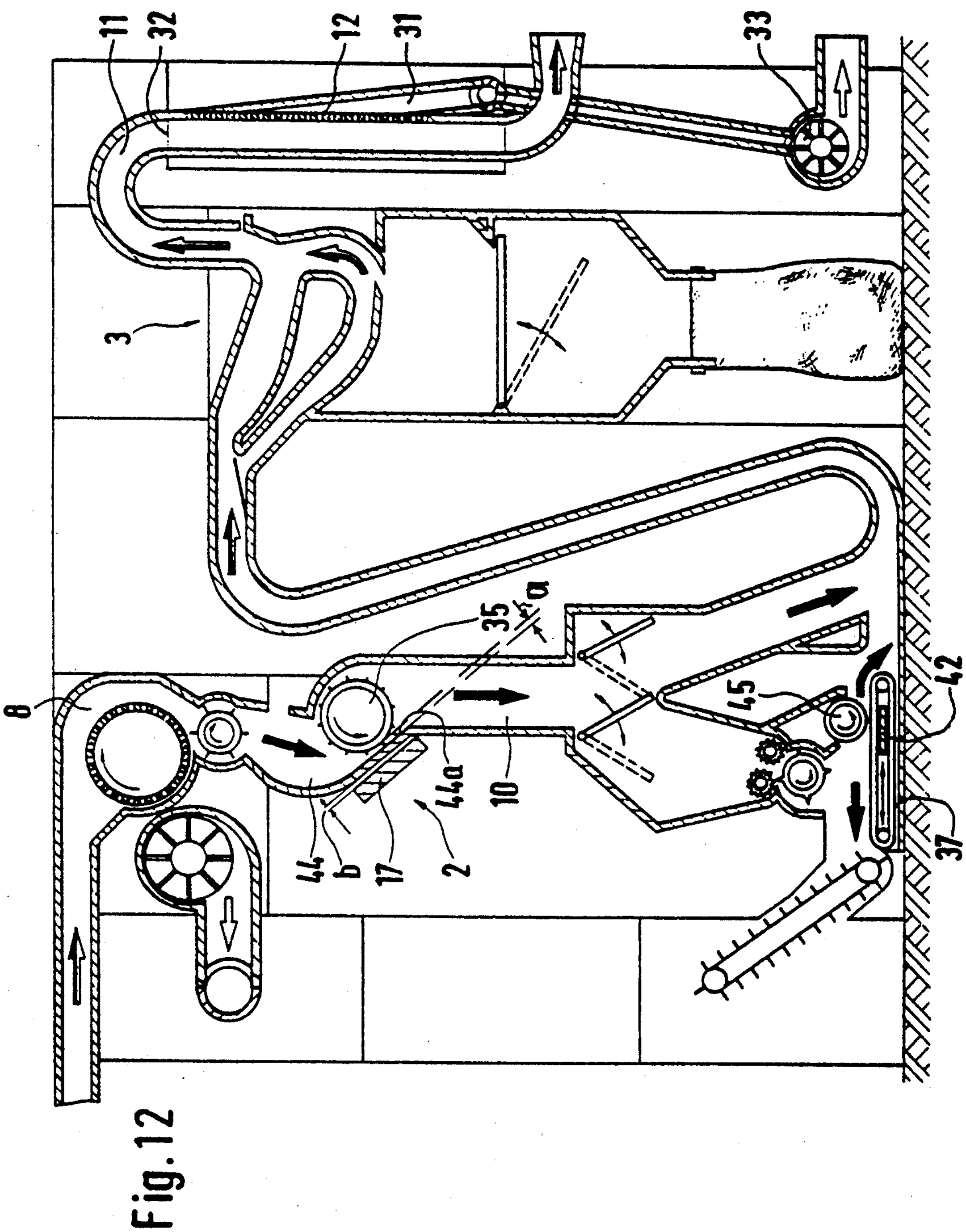
FIG. 12 is a schematic side elevational view of still another preferred embodiment of the invention.

Turning to FIG. 12, there is illustrated a further embodiment of the invention. In this embodiment, between the condenser 8 and the chute 10 a curved fiber tuft guiding channel 44 is provided. In the zone where the channel 44 merges with the inlet of the chute 10 a roll 35 is arranged which is provided with a plurality of webs 35'. The channel 44 is formed in part by a wall portion **44*a* which is made of plastic and which is spaced at a distance a from the roll 35. Underneath the chute 10 there is positioned a conveyor 37 which receives fiber material, together with the metal foreign body sensed by the detector plate 17. Between the upper reach and the lower reach of the conveyor 37 a metal detector 42 is disposed. Normally, the endless conveyor belt 37 is driven such that its upper reach travels from the left towards the right as viewed in FIG. 12. Above the upper reach of the conveyor belt 37, generally in alignment with the metal detector 42, a roll 45 is positioned. When the metal detector 42 senses the presence of a metal body on the upper reach of the conveyor belt 37, the driving mechanism of the belt 37 is reversed so that the metal body and some fiber material is moved to a waste collecting location towards the left. It is seen that in the normal, rightward travel of the upper reach of the conveyor belt 37 the material which is deposited onto the conveyor belt by the waste branch extending from the chute 10, rejoins the normal material flow beyond the right-hand end of the conveyor belt 37**.

It will be understood that the above description of the present invention is susceptible to various modifications, changes and adaptations, and the same are intended to be comprehended within the meaning and range of equivalents of the appended claims.

What is claimed is:

1. In a fiber processing line for treating fiber tufts, including a plurality of fiber processing machines, fiber duct means for serially interconnecting the fiber processing machines with one another; means for generating a stream of transporting air in said fiber duct means for pneumatically conveying the fiber tufts therein; a metal separator interposed between two fiber-processing machines, the improvement wherein said metal separator comprises (a) a generally vertical chute having an upper inlet and a lower outlet through which the fiber tufts respectively enter into and exit from the chute; a portion of said fiber duct means being coupled to the chute inlet and the chute outlet for pneumatically introducing the fiber tufts into and conveying the fiber tufts away from the chute;

(b) a metal detector positioned in said chute for detecting a metal body and emitting a sensing signal upon passage of the metal body; said metal detector being an inductive flat-surface detector and being inclined downwardly relative to horizontal;

(c) a waste discharge opening provided in said chute between said metal detector and said chute outlet;

(d) a deflecting mechanism arranged below said metal detector in said chute and having first and second positions; in the first position said deflecting mechanism guiding the stream of fiber tufts so as to proceed in said chute to and through said chute outlet and in said second position said deflecting mechanism guiding the stream of fiber tufts and metal body so as to proceed through said waste discharge opening; and (e) means for moving said deflecting mechanism from said position into said second position in response to the sensing signal emitted by said metal detector.

2. The fiber processing line as defined in claim 1, wherein said metal detector is situated substantially vertically above said deflector mechanism.

3. The fiber processing line as defined in claim 1, further comprising a guide element positioned in said chute and being inclined to the vertical for guiding the fiber tufts in the chute in an oblique path.

4. The fiber processing line as defined in claim 1, wherein said deflecting mechanism comprises a pivotally supported gate.

5. The fiber processing line as defined in claim 1, wherein said waste discharge opening is situated substantially vertically below said metal detector and further wherein in said second position of said deflecting mechanism the fiber tufts and body is guided so as to proceed to said waste discharge opening vertically without deflection.

6. The fiber processing line as defined in claim 1, wherein said waste discharge opening is situated laterally below said metal detector and further wherein in said second position of said deflecting mechanism the fiber tufts and body is guided so as to be deflected laterally downwardly toward said waste discharge opening.

7. The fiber processing line as defined in claim 1, further comprising a heavy-waste separator interconnected to the fiber processing line; a portion of said fiber duct means comprising a rising conduit coupling an output of said metal separator with an input of said heavy-waste separator; rising conduit including at least one bend.

8. The fiber processing line as defined in claim 1, further comprising a roller rotatably supported in said chute; and a downwardly inclined wall portion positioned between said roller and said detector; said roller cooperating with said wall portion for pressing thereagainst the fiber tufts passing between said roller and said detector.

9. The fiber processing line as defined in claim 8, wherein said wall portion forms a part of said chute.

10. The fiber processing line as defined in claim 8, wherein said wall portion is plastic.

11. The fiber processing line as defined in claim 8, wherein said wall portion is separated from said detector by a clearance.

12. In a fiber processing line for treating fiber tufts, including a plurality of fiber processing machines, fiber duct means for serially interconnecting the fiber processing machines with one another; means for generating a stream of transporting air in said fiber duct means for pneumatically conveying the fiber tufts therein; a metal separator interposed between two fiber-processing machines, the improvement wherein said metal separator comprises (a) a generally vertical chute having an upper inlet and a lower outlet through which the fiber tufts respectively enter into and exit from the chute; a portion of said fiber duct means being coupled to the chute inlet and the chute outlet for pneumatically introducing the fiber tufts into and conveying the fiber tufts away from the chute;

(b) a metal detector positioned in said chute for detecting a metal body and emitting a sensing signal upon passage of the metal body;

(c) a waste discharge opening provided in said chute between said metal detector and said chute outlet;

(d) a deflecting mechanism arranged below said metal detector in said chute and having first and second positions; in the first position said deflecting mechanism guiding the stream of fiber tufts so as to proceed in said chute to and through said chute outlet and in said second position said deflecting mechanism guiding the stream of fiber tufts and body so as to proceed through said waste discharge opening;

(e) means for moving said deflecting mechanism from said first position into said second position in response to the sensing signal emitted by said metal detector; and (f) two endless belts each supported by rollers in said chute and each having first and second belt portions; said first belt portions together define a flow path for the fiber tufts in a zone of said metal detector.

13. The fiber processing line as defined in claim 12, wherein said metal detector comprises an inductive coil.

14. The fiber processing line as defined in claim 12, wherein said metal detector at least partially surrounds a flow path of the fiber tufts in said chute.

15. The fiber processing line as defined in claim 12, further comprising a roller rotatably supported in said chute and cooperating with said flat-surface detector for pressing thereagainst the fiber tufts passing between the roller and the flat-surface detector.

16. The fiber processing line as defined in claim 15, wherein said roller is a plastic roller.

17. The fiber processing line as defined in claim 12, further comprising an endless belt supported by end rollers for pressing against the flat-surface detector fiber tufts passing between the belt and the flat-surface detector, said belt being inclined downwardly toward said flat-surface detector.

18. The fiber processing line as defined in claim 12, wherein said second belt portions converge downwardly with respect to one another toward said flow path defined by said first belt portions.

19. In a fiber processing line for treating fiber tufts, including a plurality of fiber processing machines, fiber duct means for serially interconnecting the fiber processing machines with one another; means for generating a stream of transporting air in said fiber duct means for pneumatically conveying the fiber tufts therein; a metal separator interposed between two fiber-processing machines, the improvement wherein said metal separator comprises (a) a generally vertical chute having an upper inlet and a lower outlet through which the fiber tufts respectively enter into and exit from the chute; a portion of said fiber duct means being coupled to the chute inlet and the chute outlet for pneumatically introducing the fiber tufts into and conveying the fiber tufts away from the chute;

(b) a metal detector position in said chute for detecting a metal body and emitting a sensing signal upon passage of the metal body;

(c) a waste discharge opening provided in said chute between said metal detector and said chute outlet;

(d) a deflecting mechanism arranged below said metal detector in said chute and having first and second positions; in the first position said deflecting mechanism guiding the stream of fiber tufts so as to proceed in said chute to and through said chute outlet and in said second position said deflecting mechanism guiding the stream of fiber tufts and body so as to proceed through said waste discharge opening;

(e) means for moving said deflecting mechanism from said first position into said second position in response to the sensing signal emitted by said metal detector;

(f) an additional chute having an upper inlet disposed below the waste discharge opening for receiving tufts and body therefrom and a lower outlet;

(g) two cooperating delivery rolls situated in said additional chute for advancing the material downwardly;

(h) an additional metal detector positioned below said delivery rolls and above the outlet of the additional chute for detecting the metal body and emitting a sensing signal upon passage of said metal body;

(i) an additional waste discharge opening provided in said additional chute between said additional metal detector and the outlet of said additional chute;

(j) an additional deflecting mechanism arranged below said additional metal detector and having first and second positions; in the first position said additional deflecting mechanism guiding the tufts so as to proceed in said additional chute to and through said outlet of said additional chute and in said second position said additional deflecting mechanism guiding the tufts and metal body so as to proceed through said additional waste discharge opening; and (k) additional means for moving said additional deflecting mechanism from said first position into said second position thereof, in response to the sensing signal emitted by said additional metal detector.

20. In a fiber processing line for treating fiber tufts, including a plurality of fiber processing machines, fiber duct means for serially interconnecting the fiber processing machines with one another; means for generating a stream of transporting air in said fiber duct means for pneumatically conveying the fiber tufts therein; a metal separator interposed between two fiber-processing machines, the improvement wherein said metal separator comprises (a) a generally vertical chute having an upper inlet and a lower outlet through which the fiber tufts respectively enter into and exit from the chute; a portion of said fiber duct means being coupled to the chute inlet and the chute outlet for pneumatically introducing the fiber tufts into and conveying the fiber tufts away from the chute;

(b) a metal detector positioned in said chute for detecting a metal body and emitting a sensing signal upon passage of the metal body;

(c) a waste discharge opening provided in said chute between said metal detector and said chute outlet;

(d) a deflecting mechanism arranged below said metal detector in said chute and having first and second positions; in the first position said deflecting mechanism guiding the stream of fiber tufts so as to proceed in said chute to and through said chute outlet and in said second position said deflecting mechanism guiding the stream of fiber tufts and metal body so as to proceed through said waste discharge opening;

(e) means for moving said deflecting mechanism from said first position into said second position in response to the sensing signal emitted by said metal detector; and (f) a heavy-waste separator interconnected to the fiber processing line downstream of the metal separator; said heavy-waste separator including means for defining a separating zone having means for defining an inlet channel opening into the separating zone for pneumatically advancing fiber material into the separating zone; and means for deflecting the fiber material upwardly to lead away the cleaned, light fiber material.

21. In a fiber processing line for treating fiber tufts, including a plurality of fiber processing machines, fiber duct means for serially interconnecting the fiber processing machines with one another; means for generating a stream of transporting air in said fiber duct means for pneumatically conveying the fiber tufts therein; a metal separator interposed between two fiber-processing machines, the improvement wherein said metal separator comprises (a) a generally vertical chute having an upper inlet and a lower outlet through which the fiber tufts respectively enter into and exit from the chute; a portion of said fiber duct means being coupled to the chute inlet and the chute outlet for pneumatically introducing the fiber tufts into and conveying the fiber tufts away from the chute;

(b) a metal detector positioned in said chute for detecting a metal body and emitting a sensing signal upon passage of the metal body;

(c) a waste discharge opening provided in said chute between said metal detector and said chute outlet;

(d) a deflecting mechanism arranged below said metal detector in said chute and having first and second positions; in the first position said deflecting mechanism guiding the stream of fiber tufts so as to proceed in said chute to and through said chute outlet and in said second position said deflecting mechanism guiding the stream of fiber tufts and metal body so as to proceed through said waste discharge opening;

(e) means for moving said deflecting mechanism from said first position into said second position in response to the sensing signal emitted by said metal detector;

(f) a conveyor including a conveyor belt having an upper reach and a lower reach; said upper reach being situated underneath said waste discharge opening for receiving tufts and metal body from said chute when said deflecting mechanism is in said second position and normally advancing the tufts and metal body in a first direction;

(g) an additional metal detector positioned between said upper and lower reaches for detecting the metal body and emitting a sensing signal upon passage of the metal body advanced on said upper reach; and (h) means for reversing a direction of motion of said conveyor in response to the sensing signal by said additional metal detector for advancing tufts and metal body on said upper reach in a second direction to a location of waste disposal.

* * * * *

UNITED STATES PATENT AND TRADEMARK OFFICE

CERTIFICATE OF CORRECTION

PATENT NO. : 5,205,019

DATED : April 27, 1993

INVENTOR(S) : Stefan Schlichter et al

It is certified that error appears in the above-identified patent and that said Letters Patent is hereby corrected as shown below:

On title page, item [19], Inventor's last name should read --Schlichter--
item [75], Inventors, 1st inventor should read --Stefan Schlichter--

Signed and Sealed this

Seventh Day of December, 1993

Attest:

BRUCE LEHMAN

Attesting Officer

*Commissioner of Patents and Trademarks*